United States Patent
Kawaguchi et al.

(10) Patent No.: US 7,637,654 B2
(45) Date of Patent: Dec. 29, 2009

(54) SPECIFIC HEAT MEASURING METHOD AND INSTRUMENT

(75) Inventors: Kenji Kawaguchi, Kyoto (JP); Masanobu Obayashi, Kyoto (JP); Nami Kurauchi, Kyoto (JP)

(73) Assignee: Kyoto Electronics Manufacturing Co., Ltd., Kyoto-shi (JP)

( * ) Notice: Subject to any disclaimer, the term of this patent is extended or adjusted under 35 U.S.C. 154(b) by 87 days.

(21) Appl. No.: 11/597,059

(22) PCT Filed: May 19, 2005

(86) PCT No.: PCT/JP2005/009175

§ 371 (c)(1),
(2), (4) Date: Jan. 29, 2007

(87) PCT Pub. No.: WO2005/114156

PCT Pub. Date: Dec. 1, 2005

(65) Prior Publication Data

US 2008/0025365 A1    Jan. 31, 2008

(30) Foreign Application Priority Data

May 21, 2004   (JP)   ............................. 2004-151978

(51) Int. Cl.
G01N 25/00   (2006.01)
G01K 17/00   (2006.01)

(52) U.S. Cl. ........................... 374/43; 374/31; 374/102; 702/136

(58) Field of Classification Search .................. 374/44, 374/43, 31, 102; 702/136
See application file for complete search history.

(56) References Cited

U.S. PATENT DOCUMENTS

| | | | | |
|---|---|---|---|---|
| 3,217,537 | A | * | 11/1965 | Hager, Jr. ..................... 374/31 |
| 4,912,962 | A |   | 4/1990  | Kawaguchi |
| 4,944,035 | A | * | 7/1990  | Aagardl et al. .............. 702/136 |

(Continued)

FOREIGN PATENT DOCUMENTS

EP         612999 A2 *   8/1994

(Continued)

OTHER PUBLICATIONS

Shepherd, Review of Scientific Instruments, vol. 56, No. 2, 1985, 2, pp. 273-277.

(Continued)

Primary Examiner—Gail Verbitsky
Assistant Examiner—Mirellys Jagan
(74) Attorney, Agent, or Firm—Birch, Stewart, Kolasch & Birch, LLP (57) ABSTRACT

In order to measure specific heat, the measurement time is very long and the instrument is very expensive. The specific heat may be calculated based on the thermal time constant obtained from the change of the sample temperature when the predetermined amount of sample with known density at the first temperature is introduced in the environment at the second temperature. This measuring method can use the oscillatory densitometer. The predetermined amount corresponds to the volume of the sample to be introduced in the oscillatory densitometer, the density is a measurement result of the oscillatory densitometer, and the thermal time constant corresponds to the time constant of the oscillation period of the oscillatory densitometer.

9 Claims, 8 Drawing Sheets

U.S. PATENT DOCUMENTS

| | | | | |
|---|---|---|---|---|
| 4,956,793 | A | * | 9/1990 | Bonne et al. .................. 702/50 |
| 5,038,304 | A | * | 8/1991 | Bonne ......................... 702/99 |
| 5,311,447 | A | * | 5/1994 | Bonne ......................... 702/50 |
| 5,711,604 | A | * | 1/1998 | Nakamura .................. 374/44 |
| 5,988,875 | A | * | 11/1999 | Gershfeld et al. ............. 374/10 |
| 6,019,505 | A | * | 2/2000 | Bonne et al. .................. 374/40 |
| 6,071,008 | A | * | 6/2000 | Hatta et al. ................... 374/31 |
| 6,913,383 | B2 | * | 7/2005 | Jorimann et al. .............. 374/31 |
| 2005/0002436 | A1 | * | 1/2005 | Taketoshi et al. ............. 374/43 |
| 2007/0286254 | A1 | * | 12/2007 | Fon et al. ..................... 374/31 |

FOREIGN PATENT DOCUMENTS

| | | | |
|---|---|---|---|
| JP | 57206839 | A * | 12/1982 |
| JP | 7-104249 | B2 | 11/1995 |
| JP | 10213558 | A * | 8/1998 |
| JP | 3380903 | B2 | 12/2002 |

OTHER PUBLICATIONS

Y Saitoh, "Foundation of Thermal Analysis for Materials Science," Kyoritsu Publishing Co., Ltd., Third Printing of First Edition: Oct. 5, 1996.

* cited by examiner

FIG. 7(b) ENLARGED VIEW

SPECIFIC HEAT MEASURING METHOD AND INSTRUMENT

FIELD OF THE INVENTION

This invention relates to a method of measuring specific heat and an instrument thereof, and more specifically relates to a specific heat measuring method and instrument using thermal time constant.

DESCRIPTION OF THE RELATED ART

Figure 8:
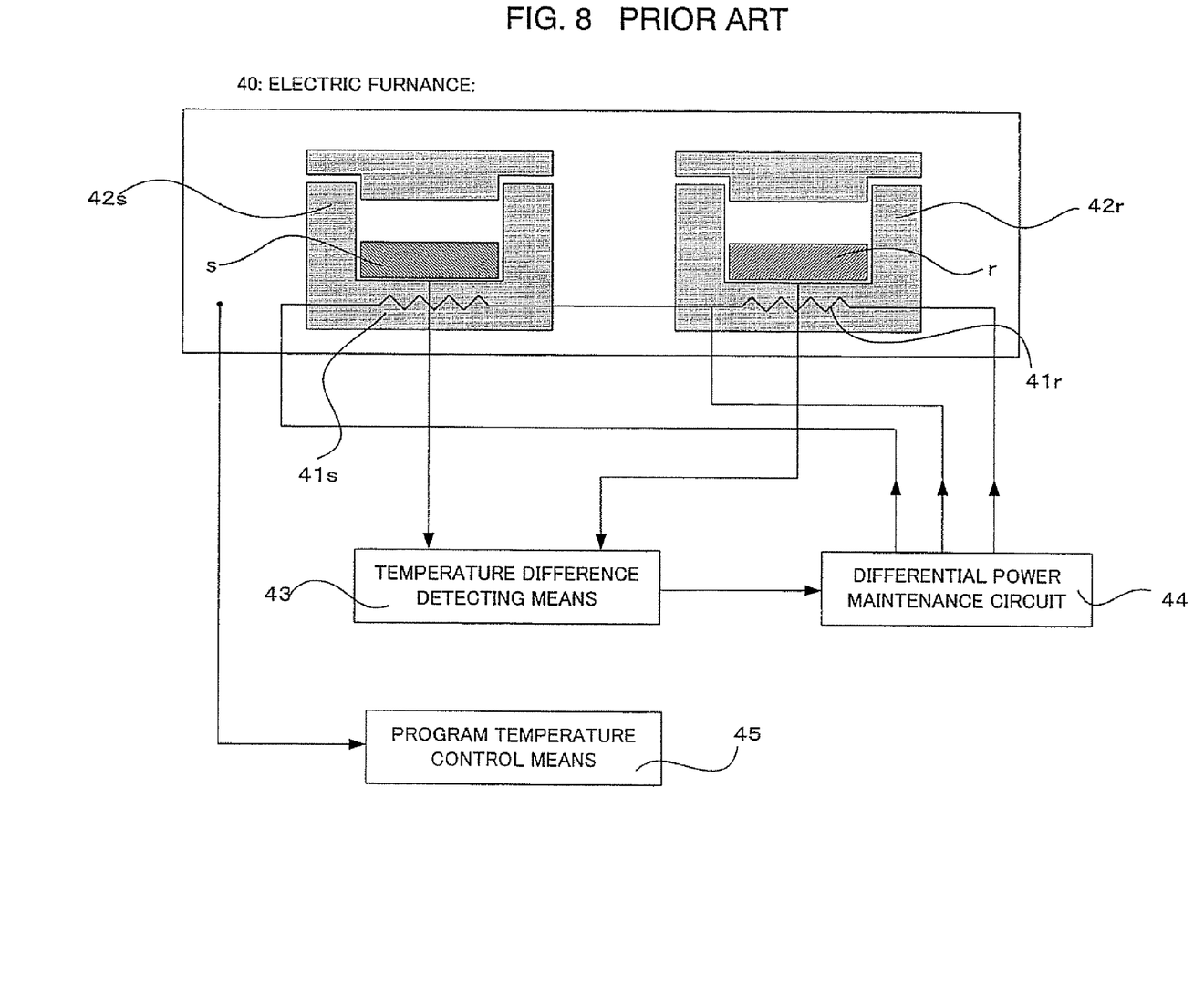
FIG. 8 is a diagram of prior art.

The measurement of specific heat has been performed by a large-scale instrument. For instance, in a differential scanning calorimeter, a reference material r and a sample s are placed in holders 42r and 42s in an electric furnace 40, and a program temperature control means 45 heats the electric furnace so that the rate of the temperature increasing is kept at a constant, as shown in FIG. 8. The temperature difference between the sample s and the reference material r is detected by a temperature difference detecting means 43. In order to keep the temperature difference "0" a differential power compensation circuit 44 controls heaters 41r and 41s to heat the electric furnace.

Under such configuration, the specific heat of the sample s is found in consideration of heat flow rates of the sample s and the reference material r in the holders 42s and 42r ("Foundation of Thermal Analysis for Materials Science" written by Yasutoshi Saitoh, Kyoritsu Publishing Co., Ltd., Oct. 5, 1996).

SUMMARY OF THE INVENTION

However, there are disadvantages in the above-mentioned instrument; the configuration gets large scale; it takes a very long time to find the specific heat for one sample; and, both the instrument cost and the personal expense become expensive.

The invention is suggested in view of the above-mentioned problems, and it has an object to provide a specific heat instrument of which cost is very low and that requires a very short measurement time.

The present invention is characterized that a predetermined amount of sample with known density at a first temperature is introduced to an environment of a second temperature, a thermal time constant is obtained from a change of the sample temperature with time in the environment of the second temperature, and a specific heat is calculated by the obtained thermal time constant.

The specific heat can be calculated by means of an oscillatory densitometer. That is to say, the predetermined amount of sample corresponds to an amount of sample to be introduced in a capillary tube (measurement cell) of the oscillatory densitometer, and the change of the sample temperature corresponds to the change of the oscillation period of the capillary tube. The density is a measurement result of the oscillatory densitometer, and the thermal time constant is allowed to correspond to a time constant of the oscillation period of the capillary tube of the oscillatory densitometer. The time constant can be found in process of calculating the density by a calculating unit.

In another aspect of the present invention, it may be configured to calculate the specific heat of the sample based on the response of the sample temperature detected as follows. The response of the sample temperature with change of the environment temperature is detected, when the predetermined amount of sample with known density is placed in an environment at the first temperature.

In this case, the measurement cell corresponds to the capillary tube of the oscillatory densitometer holding the sample of the predetermined amount, and the density is the result calculated by the calculating unit of the oscillatory densitometer. A temperature measuring unit corresponds to the period detecting unit of the oscillatory densitometer, the sample temperature corresponds to an oscillation period of the capillary tube, and the calculating unit corresponds to a calculating unit of the oscillatory densitometer, and the change of the sample temperature corresponds to a phase change of the oscillation period.

The present invention makes it possible to measure the specific heat of sample in a very simple manner. Since the specific heat can be measured by a very simple configuration of instrument, it is possible to reduce the instrument cost extremely. In addition, the oscillatory densitometer can measure the specific heat and the density simultaneously.

DETAILED DESCRIPTION OF THE INVENTION

Figure 1:
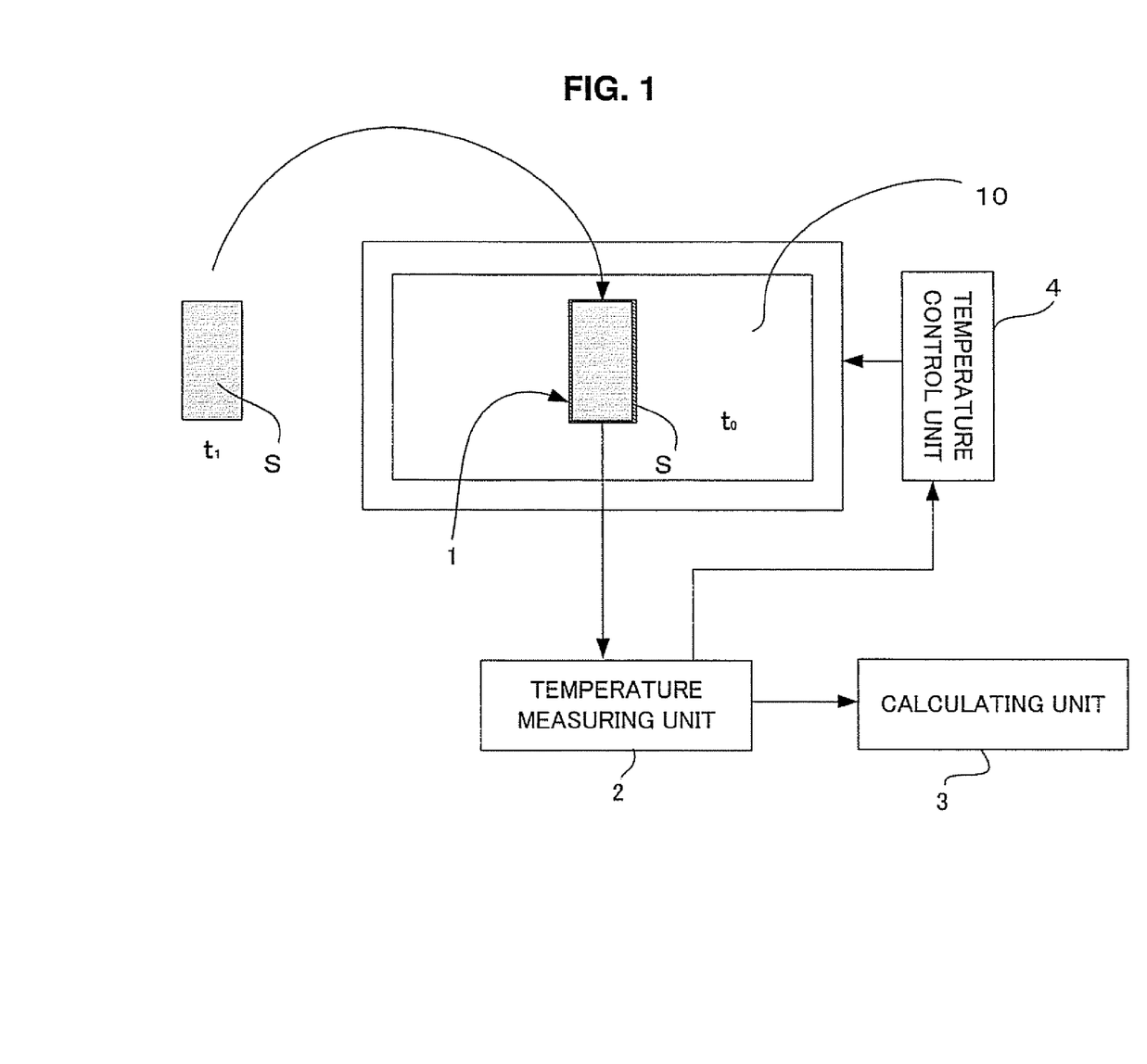
FIG. 1 is a diagram explaining a principle of the invention.

FIG. 1 is a diagram explaining a principle of the invention.

A predetermined amount of sample at a first temperature $t_1$ is introduced in a measurement cell 1 of a measurement chamber 10, of which temperature is controlled to a second temperature $t_0$ being different from the first temperature $t_1$, and a change of the sample temperature is measured by a temperature measuring unit 2. With the assumption that a temperature control unit 4 keeps the temperature of the measurement chamber 10 at the above temperature $t_0$, the temperature of the sample starts to vary (increase or decrease) to an endpoint temperature that is the second temperature $t_0$, depending on the time constant. A calculating unit 3 calculates the time constant based on the change of the sample temperature obtained by the temperature measurement unit 2, and its result depends on a material of the sample.

As a matter of course, it can be assumed that, in case of the same density of materials, the larger the specific heat is, the slower the degree of the temperature gradient gets. And in case of the same specific heat of the materials, the larger the density is, the slower the degree of the temperature gradient gets. It is not difficult to understand that the time constant is concerned with the specific heat and the density.

Figure 2:
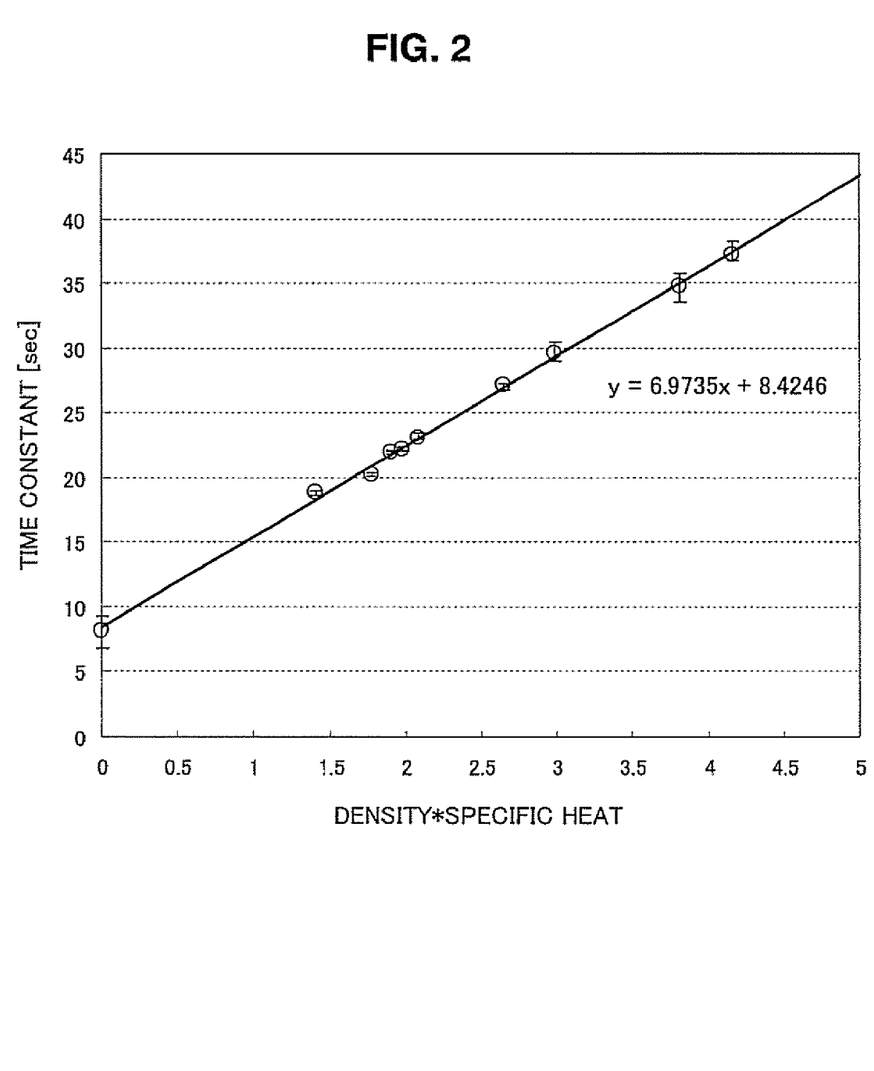
FIG. 2 is a graph of time constant vs. density × specific heat.

Therefore, in case of the material (gas and liquid) of which specific heat and density are known, a graph in which the specific heat × the density is set to a horizontal axis and the time constant at the temperature increase (decrease) is set to the vertical axis shows a straight line as shown in FIG. 2. At this time, the change of the sample temperature is measured after the sample at the temperature $t_1$ is introduced into the environment at temperature $t_0$, and the time constant is found from the detected change of the sample temperature with time. However, the time constant can be found from the change of an oscillation period of the oscillatory densitometer as described below.

If an equation to express the straight line shown in FIG. 2 is known, the specific heat can be calculated by finding values of the thermal time constant and the density. Where $x_{H2O}$ represents the specific heat of water, $d_{H2O}$ represents the density of water, $x_{air}$ represents the specific heat of air, and $d_{air}$ represents the density of air, the straight line shown in FIG. 2 is given by an equation (1).

(Equation 1)

$$\tau = \frac{\tau_{H2O} - \tau_{air}}{x_{H2O}d_{H2O} - x_{air}d_{air}} xd + \tau_0 \quad (1)$$

As the specific heat x and the density d of air and water respectively are shown in table 1, the equation (1) is defined to equations (2) and (3).

TABLE 1

| Sample | Specific heat x (JK$^{-1}$g$^{-1}$) | Time constant τ (sec) |
| --- | --- | --- |
| Air | 1.0165 (300 K) | 8.12 |
| Water | 4.1782 (30° C.) | 37.25 |

(Equation 2)

$$\tau = 7.00422xd + 8.11173 \quad (2)$$

In result, an equation (3) to find the specific heat is obtained by the time constant τ and the density d that are obtained by the measurement.

(Equation 3)

$$x = \frac{\tau - 8.11173}{7.00422d} \quad (3)$$

Figure 3:
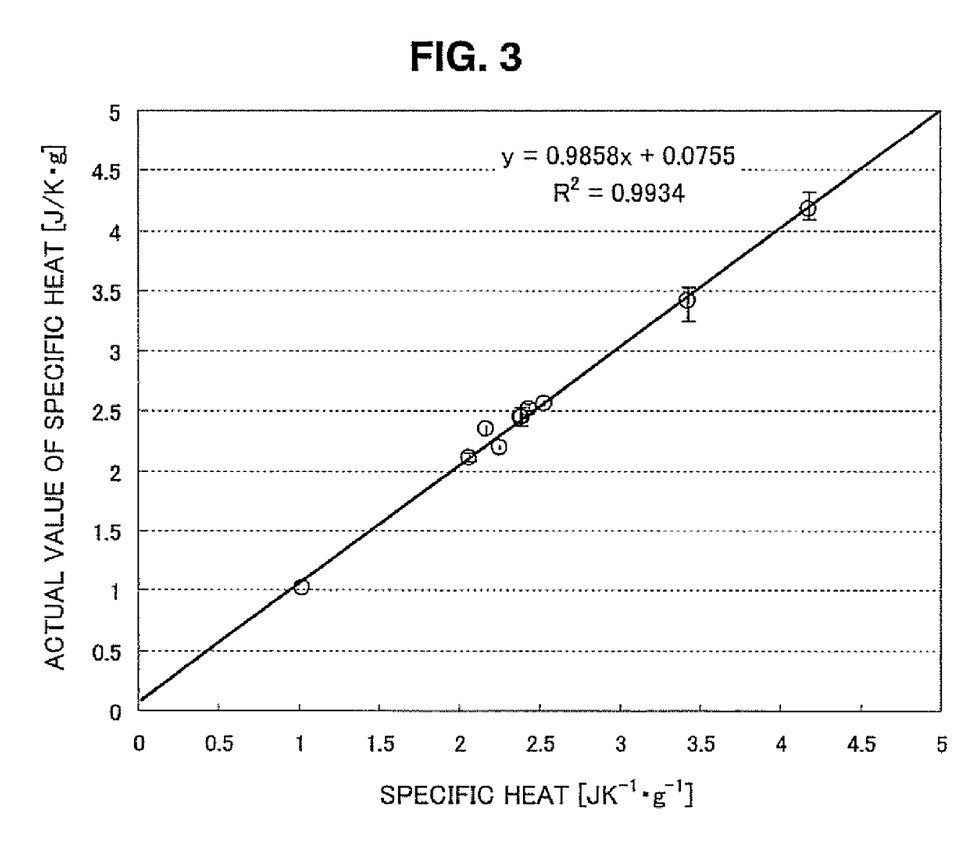
FIG. 3 is a graph of actual measured value of specific heat vs. specific heat.

Using an actual measured density d and a detected time constant τ to the above equation (3), each specific heat of various liquids can be calculated. The calculated results are shown in a left column of Table 2 as "actual measured value x" while the specific heats defined by the technical literature are shown in a right column of Table 2. A graph, representing the specific heat defined by the technical literatures and the calculated specific heats, is shown in FIG. 3. It is obvious that the specific heat found by the method in the present invention corresponds to the specific heat in the technical literature.

TABLE 2

Calculation Result of Specific Heat

| Sample Name | Specific heat (JK$^{-1}$g$^{-1}$) | Density d (gcm$^{-3}$) | Time constant τ(sec) | Actual Measured Value x (Jg$^{-1}$K$^{-1}$) |
| --- | --- | --- | --- | --- |
| Air | 1.02 | 0.00116 | 8.12 | 1.016 |
| Methanol | 2.53 | 0.78182 | 22.18 | 2.569 |
| Ethanol | 2.44 | 0.78083 | 21.92 | 2.525 |
| Hexane | 2.17 | 0.65155 | 18.86 | 2.355 |
| Acetone | 2.26 | 0.78533 | 20.18 | 2.194 |
| Degassed pure water | 4.18 | 0.99567 | 37.25 | 4.178 |
| Ethylene glycol | 2.39 | 1.10627 | 27.10 | 2.451 |
| Aniline | 2.06 | 1.01309 | 23.04 | 2.104 |
| Glycerin | 2.38 | 1.25558 | 29.65 | 2.449 |
| Glycerin Solution | 3.42 | 1.11540 | 34.74 | 3.408 |

Figure 4:
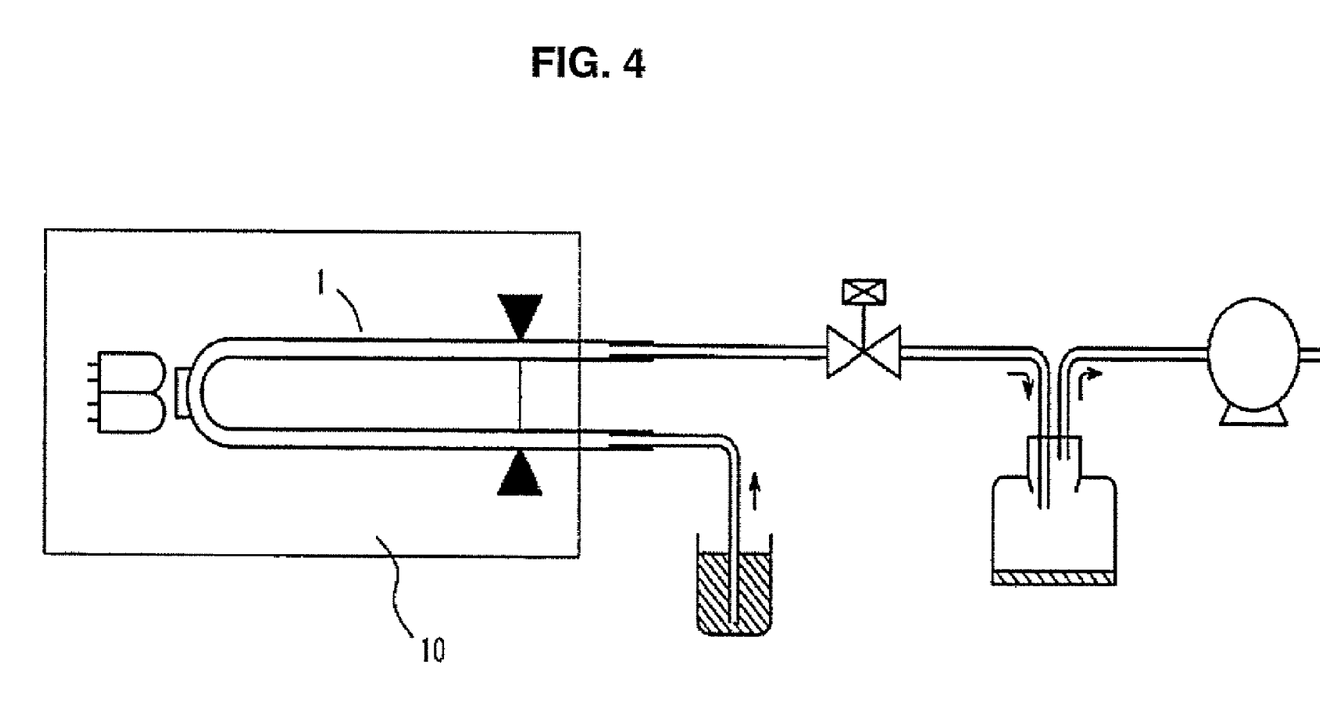
FIG. 4 is a conceptual diagram of oscillatory densitometer.
Figure 5:
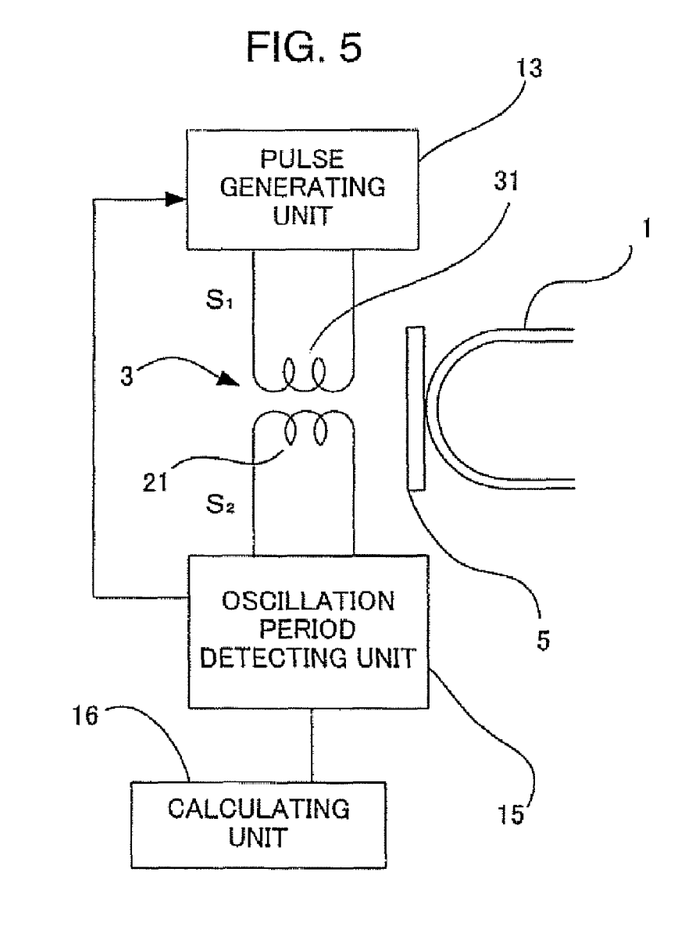
FIG. 5 is a block diagram showing circuits of the oscillatory densitometer.

Japanese Patent No. 2,061,924, of which applicant is the same this invention, discloses a oscillatory densitometer as shown in FIG. 4 and FIG. 5 that is configured as follows.

It is configured that a U-shaped capillary tube 1 forming the measurement cell is provided to the measurement chamber 10 to allow a predetermined amount of liquid or gas sample to be introduced in the U-shaped capillary tube.

When a drive pulse current S2 is provided from a pulse generator 13 to a driving coil 31, an external force is given to the capillary tube 1 through a magnetic material 4 equipped at a tip of the capillary tube 1, and the capillary tube 1 starts to oscillate. A period detecting unit 15 processes a sine wave S$_2$ generating at a detecting coil 21 in response to the oscillation, and finds an oscillation period of the capillary tube 1. According to the result, a calculation unit 16 finds the density of the sample. Besides, the drive current S$_1$ is given at a predetermined time interval synchronizing with the detected sine wave S$_2$.

A driving unit 3 (the driving coil 31 and the magnetic material 4) gives the driving force to the capillary tube 1, while keeping the temperature of the measurement chamber 10 at a predetermined temperature $t_0$ (the second temperature), (as a mater of course, the sample temperature is also kept at the second temperature $t_0$). According to the natural oscillation period $T_0$ at this time, the density d can be found by following equation (4).

(Equation 4)

$$d_x = d_A - \frac{T_A^2 - T_x^2}{T_A^2 - T_B^2}(d_A - d_B) \quad (4)$$

$d_x$: density of sample
$d_A$: density of reference material A
$d_B$: density of reference material B
$T_x$: oscillation period of sample
$T_A$: oscillation period of sample A
$T_B$: oscillation period of sample B When the sample at the first temperature $t_1$ is introduced in the measurement chamber 10 of which temperature is kept at the other temperature $t_0$, the sample temperature varies from the first temperature $t_1$ to the second temperature $t_0$ according to a predetermined constant. At this time, the oscillation period also varies together with the change of temperature, and it is sure that the change of oscillation period depends on the predetermined time constant.

Therefore, the time constant that defines the change of the temperature from the first temperature $t_1$ to the second temperature $t_0$ can be found by measuring the change of the oscillation period of the capillary tube 1.

The oscillation period at the second temperature $t_0$ cannot be found only at the second temperature $t_0$. By measuring the change of the oscillation period (the change of temperature) after the sample at the first temperature $t_1$ is introduced in the capillary tube 1, the oscillation period can be calculated even not at the second temperature $t_0$. The calculation method thereof is disclosed in details in Japanese Patent No. 2,061,924 (Japanese Patent Publication No. 07-104249 A) which was patented by the applicant.

That is to say, the temperature t of the sample introduced in the measurement chamber 1 varies depending on a time s, as defined in equation (5).

(Equation 5)

$$t = t_0\left(1 - e^{\frac{t_x - s}{\tau_x}}\right) \quad (5)$$

$t_0$: convergence temperature
$\tau_x$: time constant depending on sample
$t_x$: constant depending on a first temperature of sample From the change of temperature, it is possible to analogize that the period T varies as expressed in equation (6). The validity of the analogical interpretation is based on the description in Japanese Patent Publication No. 07-104249A.

(Equation 6)

$$T = T_0\left(1 - e^{\frac{t_T - s}{\tau_T}}\right) \quad (6)$$

$T_0$: convergence period
$\tau_t$: time constant depending on sample
$t_T$: constant depending on a first temperature of sample By differentiating the both sides of the equation (6), following equation is obtained.

(Equation 7)

$$T' = \alpha T + \beta \quad (7)$$

where, $$\alpha = -\frac{1}{\tau_T} \quad \beta = -\frac{T_0}{\tau_T}$$

According to the above equation, the oscillation period detecting unit 15 detects an oscillation period T at the time s after the sample is introduced in the capillary tube 1, and the calculation unit 16 determines α based on the oscillation period T and the differentiated value using the least square method. From the α value, the time constant can be determined.

Since the instrument is an oscillatory densitometer, it is able to detect the density at the same time. In addition, since the introduced volume of the sample is fixed, it is possible to obtain all the necessary data at the same time.

As described above, the specific heat can be found from the time constant corresponding to the change of the sample temperature under the environment, and the time constant can be found from a phase difference between the environment temperature and the sample temperature when the environment temperature varies periodically.

Figure 6:
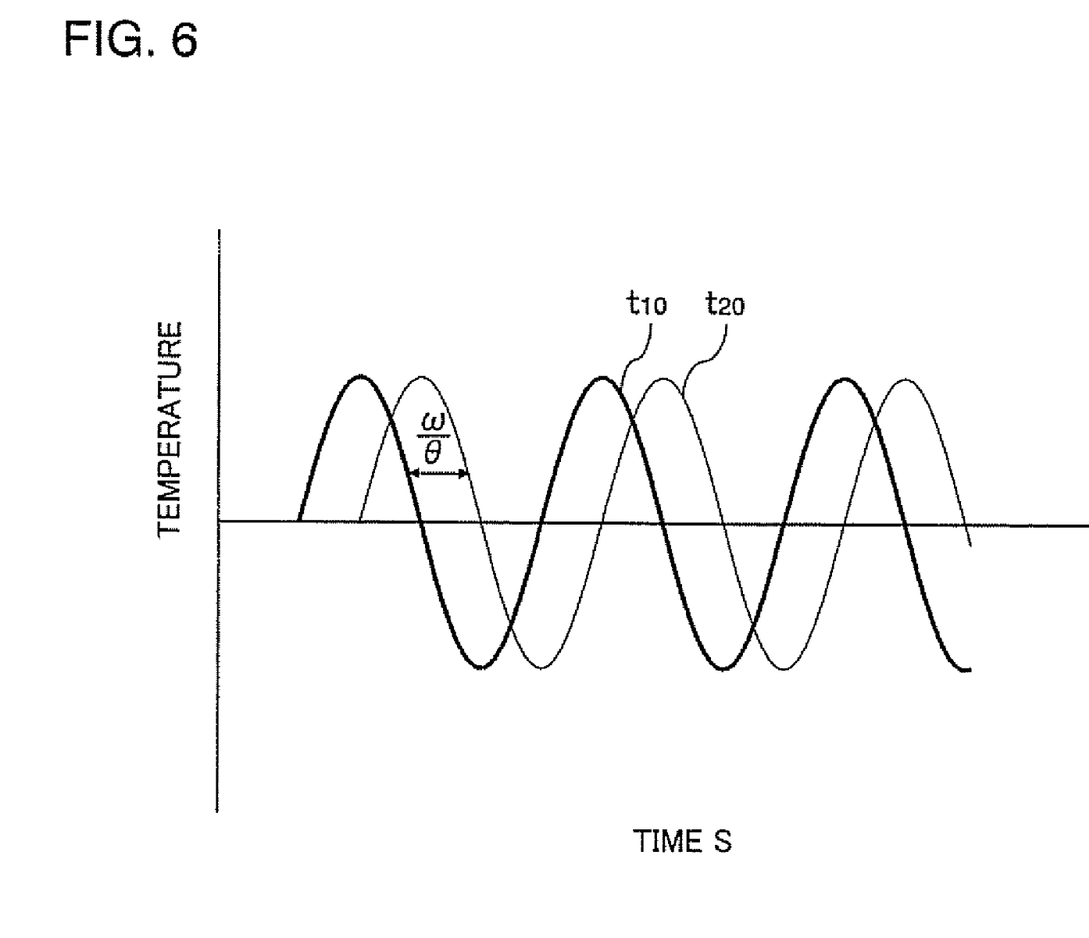
FIG. 6 is a diagram showing a phase difference between an environment temperature and a sample temperature.

In other words, as shown in FIG. 6, when a very little periodical change of temperature is given to a fixed environment temperature $t_{10}$, the sample temperature $t_{20}$ varies following to the environment temperature $t_{10}$, and a phase difference θ is observed between the environment temperature $t_{10}$ and the sample temperature $t_{20}$.

The relation between the phase difference θ and the time constant τ becomes $\theta = -\tan^{-1}(\omega\tau)$. Based on this relation, the time constant τ can be found. In this case, as described in the aforementioned first embodiment, if the sample temperature $t_{20}$ is not set to be different from the environment temperature $t_{10}$ in advance, the time constant τ can be found.

Figure 7A:
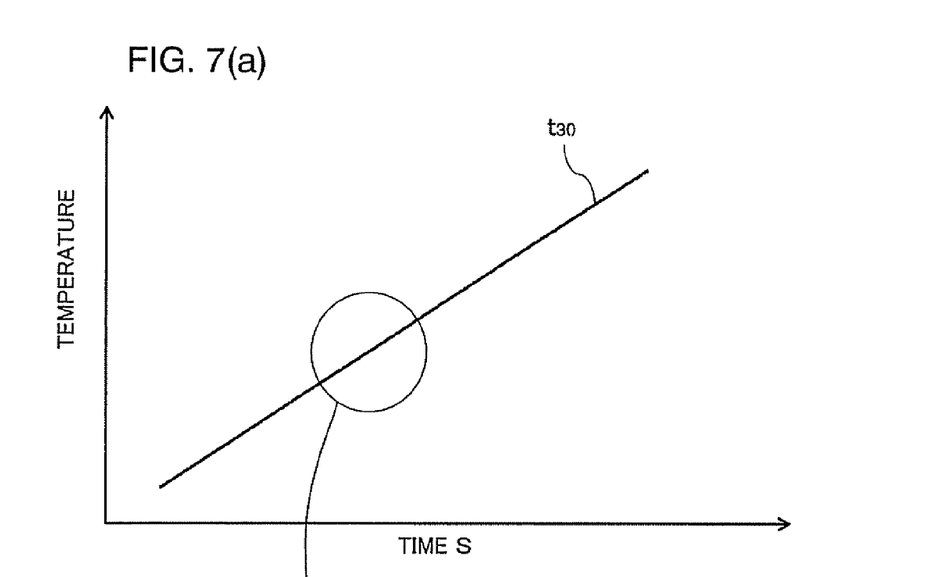
FIG. 7 is a diagram showing a phase difference between an environment temperature and a sample temperature.
Figure 7B:
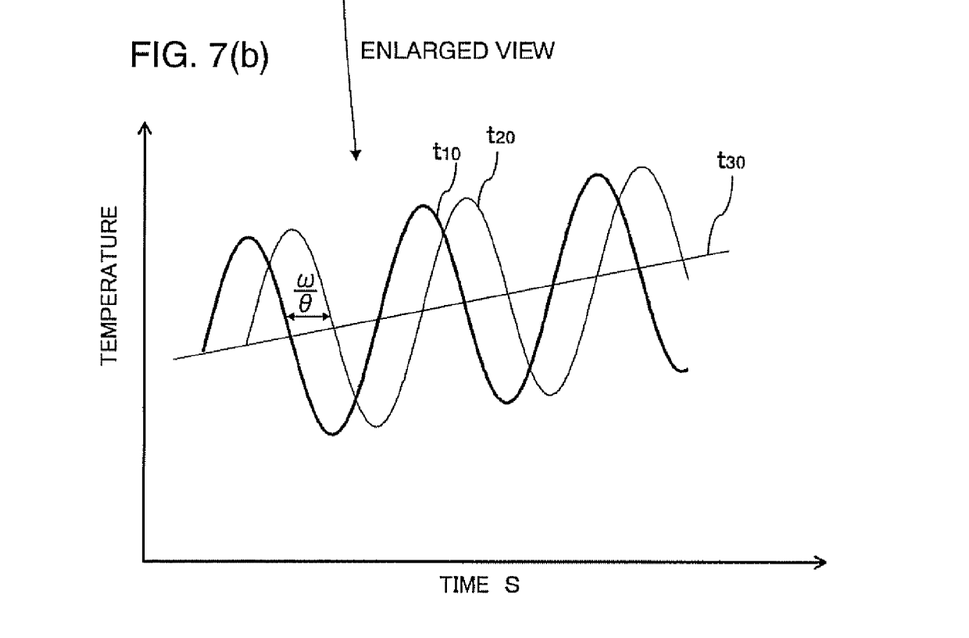

In addition, as shown in FIG. 7(*a*) and FIG. 7(*b*), as well as a very small periodical change of temperature is given to the environment temperature $t_{10}$, a center temperature $t_{30}$ varies continuously with slower pace more than the periodical change, it is possible to continuously measure the specific heat at each temperature.

In the above two cases, the oscillatory densitometer can be used. That is to say, the environment temperature $t_{10}$ can be obtained by varying a control temperature of the measurement chamber. Since the oscillation period T of the capillary tube depends on the sample temperature $t_{20}$ at that time, the change of the sample temperature $t_{20}$ can be obtained by finding the change of the oscillation period T. Therefore, the phase difference between the environment temperature $t_{10}$ and the sample temperature $t_{20}$ can be obtained from the change of the phase difference of the oscillation period T of the capillary tube 1.

What is claimed is:

1. A specific heat measuring method comprising:
   introducing a predetermined amount of sample with known density at a first temperature into an environment at a second temperature;
   obtaining a thermal time constant from a change with time of sample temperature in the environment at the second temperature; and
   calculating a specific heat based on the thermal time constant and on said density,
   wherein the predetermined amount of sample corresponds to a volume of sample to be introduced into an oscillatory densitometer, the density is a measurement result of the oscillatory densitometer, and the thermal time constant corresponds to a time constant of oscillation period of the oscillatory densitometer.

2. A specific heat measuring method according to claim 1, wherein said thermal time constant is linearly related to a product between said specific heat and said density.

3. A specific heat measuring method comprising:
   placing a predetermined amount of sample with known density into an environment at a first temperature;
   detecting a change of the sample temperature when the temperature of the environment varies; and
   calculating a specific heat of the sample based on the change of the sample temperature in the environment and based on said density,
   wherein the specific volume corresponds to a volume of sample to be introduced into an oscillatory densitometer, the density is a measurement result of the oscillatory densitometer, and the variation of sample temperature corresponds to the change of the oscillation period of the oscillatory densitometer depending on the change of environment temperature.

4. A specific heat measuring method according to claim 3, wherein said specific heat is calculated using a time constant that is determined from a phase difference between the environment temperature and the sample temperature when the environment temperature varies periodically.

5. A specific heat measuring instrument comprising:
a measurement cell holding a predetermined amount of sample with a predetermined density;
a measurement chamber provided with the measurement cell therein and of which inside temperature is controlled at a predetermined temperature;
a temperature measuring unit measuring a change of the sample temperature with time when the sample at a first temperature is introduced into the measurement cell controlled at a second temperature; and
a calculating unit calculating a specific heat based on a thermal time constant of the sample obtained from the change of the sample temperature with time and based on said density,
wherein the measurement cell corresponds to a capillary tube of an oscillatory densitometer holding the predetermined amount of sample, the density is a result calculated by a calculating unit of the oscillatory densitometer, the temperature measuring unit corresponds to a period detecting unit of the oscillatory densitometer, the sample temperature corresponds to a oscillation period of the capillary tube, the calculating unit corresponds to a calculating unit of the oscillatory densitometer, and the thermal time constant corresponds to a time constant of the oscillation period.

6. A specific heat measurement instrument according to claim 5, wherein said thermal time constant is linearly related to a product between said specific heat and said density.

7. A specific heat measurement instrument comprising:
a measurement cell holding a predetermined amount of sample with a predetermined density;
a measurement chamber provided with the measurement cell therein and of which inside temperature is controlled;
a temperature measuring unit measuring a change of the sample temperature with time when the sample is introduced into the measurement cell and the temperature of the measurement cell varies; and
a calculating unit calculating a specific heat based on the change of the sample temperature with time when the temperature of the measurement cell varies and based on said density,
wherein the measurement cell corresponds to a capillary tube of an oscillatory densitometer holding the predetermined amount of sample, the density is a result calculated by a calculating unit of the oscillatory densitometer, the temperature measuring unit corresponds to a period detecting unit of the oscillatory densitometer, the sample temperature corresponds to an oscillation period of the capillary tube, the calculating unit corresponds to a calculating unit of the oscillatory densitometer, and the change of the sample temperature with time corresponds to a phase change of the oscillation period.

8. A specific heat measurement instrument according to claim 7, wherein said specific heat is calculated using a time constant that is determined from a phase difference between the environment temperature and the sample temperature when the measurement cell temperature varies periodically.

9. A specific heat measuring method comprising:
introducing a predetermined amount of sample with known density at a first temperature into an environment at a second temperature;
obtaining a thermal time constant from a change with time of sample temperature in the environment at the second temperature; and
calculating a specific heat based on a linear relationship between the thermal time constant, and the density multiplied by the specific heat.

* * * * *